(12) United States Patent
Colombo et al.

(10) Patent No.: US 6,913,779 B2
(45) Date of Patent: Jul. 5, 2005

(54) PROCESS FOR THE PREPARATION OF ACCELERATED RELEASE FORMULATIONS USING COMPRESSED FLUIDS

(75) Inventors: Italo Colombo, Inzago (IT); Paolo Pallado, Padua (IT)

(73) Assignee: Eurand International S.p.A. (IT)

( * ) Notice: Subject to any disclaimer, the term of this patent is extended or adjusted under 35 U.S.C. 154(b) by 0 days.

(21) Appl. No.: 10/221,704

(22) PCT Filed: Mar. 7, 2001

(86) PCT No.: PCT/EP01/02538

§ 371 (c)(1),
(2), (4) Date: Feb. 26, 2003

(87) PCT Pub. No.: WO01/68054

PCT Pub. Date: Sep. 20, 2001

(65) Prior Publication Data

US 2003/0161957 A1 Aug. 28, 2003

(30) Foreign Application Priority Data

Mar. 17, 2000 (IT) .................................... MI2000A0560

(51) Int. Cl.$^7$ ............................ B05D 3/00; A61K 9/14; A61K 9/16
(52) U.S. Cl. ...................... 427/2.24; 427/2.1; 427/2.14; 427/372.2; 427/2.3; 427/244; 427/407.1; 427/409
(58) Field of Search ............................. 427/372.2, 2.1, 427/2.14, 2.24, 2.3, 244, 407.1, 409

(56) References Cited

U.S. PATENT DOCUMENTS

| | | | | |
|---|---|---|---|---|
| 5,128,142 A | * | 7/1992 | Mulligan et al. | 424/457 |
| 5,340,614 A | * | 8/1994 | Perman et al. | 427/2.24 |
| 6,214,384 B1 | * | 4/2001 | Pallado et al. | 424/493 |
| 6,627,246 B2 | * | 9/2003 | Mehta et al. | 427/2.1 |

FOREIGN PATENT DOCUMENTS

EP       0 405 284 A2  *  1/1991          A61L/29/00

OTHER PUBLICATIONS

Benedetti, et al., "Communication to the Editor. Production of Micronic Particles of Biocompatible Polymer Using Supercritical Carbon Dioxide," *Biotechnology and Bioengineering*, vol. 53, pp. 232–237 (1997).

* cited by examiner

*Primary Examiner*—Jennifer Michener
(74) *Attorney, Agent, or Firm*—Thompson Hine LLP

(57) ABSTRACT

The following description refers to a process for the impregnation of cross-linked polymers with an active ingredient. The process is based on the used of compressed fluids, in particular $CO_2$, with antisolvent effect, and involves the steps of impregnating the polymer with an active ingredient solution, adding a compressed fluid until precipitation of the active ingredient caused by the compressed fluid antisolvent effect, removing the solvent and the compressed fluid. The process allows to obtain accelerated release pharmaceutical formulations that, compared with the formulations already known, contain larger quantities of amorphous or nanocrystalline active ingredient.

14 Claims, 7 Drawing Sheets

PROCESS FOR THE PREPARATION OF ACCELERATED RELEASE FORMULATIONS USING COMPRESSED FLUIDS

FIELD OF THE INVENTION

The present invention refers to accelerated release formulations. The process for the preparation of same consists in the impregnation of cross-linked polymers with an active ingredient and is based on the use of compressed fluids, in particular compressed $CO_2$, under controlled temperature and pressure conditions. The process allows to obtain accelerated release pharmaceutical formulations containing amorphous or nanocrystalline active ingredient in large quantities.

PRIOR ART

The need for accelerating the action of oral drugs has been felt for a long time. To this end, accelerated release pharmaceutical formulations that, compared with the traditional ones, exert a quicker and more intense therapeutic action, are proposed. Accelerated release formulations essentially contain an active ingredient combined with a carrier that quickly dissolves in the gastrointestinal tract, thus accelerating the active ingredient release rate. The carrier usually consists of highly soluble substances or contains disgregating agents or other systems that facilitate a rapid dissolution of the pharmaceutical form.

However, in the case of drugs having low solubility in the gastrointestinal tract, said approach is little effective since the drug fraction that passes into solution (i.e. absorbable from the body) is low, in spite of all efforts made to accelerate the active ingredient release from the formulation.

In that case, the therapeutic action is accelerated by modifying the active ingredient physical form, in particular by preventing or limiting the aggregation into a crystalline form. As concerns many substances, the aggregation into a crystalline form hinders the quick dissolution of the active ingredient, since the dissolution of a crystalline lattice (see FIG. 1), compared to that of the corresponding amorphous form, involves significant energy consumption. Unfortunately, many substances spontaneously aggregate into a crystalline form: typical examples are the drugs of biopharmaceutical class II, as defined in "Guidance for Industry: Immediate Release Solid Oral Dosage Forms", Center for Drug Evaluation and Research at the Food and Drug Administration, 1997. Although said drugs once in solution can be easily absorbed from the intestine, they are characterised by hardly soluble crystalline structures. In such cases the crystalline aggregation is to be modified, either wholly or partially, by convenient processes and formulations that favour the formation of a disordered structure typical of amorphous forms and/or of a more soluble nanocrystalline structure.

Some processes obtain small-sized particles by causing the active ingredient to precipitate into polymeric matrices (impregnation processes). According to said processes, the active ingredient is dissolved in a solvent and the resulting solution is used for polymer impregnation. After gradual solvent evaporation, the active ingredient precipitates and impregnates the polymer. Compared with free-form precipitation, the precipitation into the polymer network limits the molecules capability to aggregate and, therefore, allows a more significant micronisation of the precipitated active ingredient. However, said technique results in a considerable approximation of the particle size uniformity and of the precipitated particles stability.

U.S. Pat. No. 5,222,192 discloses the obtainment of a large portion of amorphous drug by polymer impregnation, according to techniques known in the art, followed by the treatment of the impregnated polymer with solvent vapour: however, the treatment in a vapour environment requires a longer production cycle and poses stability problems for the active ingredients.

In patent WO 99/25322 the polymer impregnation technique is partially modified by substituting supercritical fluid for traditional solvents.

By supercritical fluid (SCF) it is meant a low molecular weight fluid having a critical temperature $T_C$ close to room temperature ($T_C$=10 to 40° C. approx.) and a not too high critical pressure $P_C$ ($P_C$=40 to 75 bar). Exemplary substances that form supercritical fluids are light hydrocarbons and some chlorofluorocarbons. The most important example of SCF is carbon dioxide ($P_C$=72.1 bar) which exhibits excellent properties, such as non-inflammability, environmental acceptability, non-toxicity, low cost even at high purity.

In the aforesaid patent WO 99/25322, the solvent used for the active ingredient is supercritical $CO_2$. The resulting solution is contacted with the polymer, and the drug is partitioned between solution and polymer; the solution is removed and the partitioned active ingredient remains deposited in the polymer. However, a limiting factor of this process is inherent in the partition phenomenon. In fact, only the drugs securing a high level of molecular interaction with the polymer may guarantee high impregnation levels.

Supercritical fluids are also used for the free-form precipitation of active ingredients insoluble in the fluid itself and dissolved in traditional solvents. Said technique is based on the spraying of active ingredient solutions in a reactor saturated with a supercritical fluid, followed by precipitation of the active ingredient in the fine form. Said technique was also suggested for the precipitation of mixed polymer-active ingredient solutions to obtain active ingredient-loaded polymeric microspheres (Biotech. Bioeng., 53, 232–238, 1997).

In summary, the processes of polymer impregnation known in the art, based on the use of traditional or supercritical solvents are not wholly satisfactory: in particular, they suffer from the disadvantage of providing a non-uniform dispersion of the active ingredient in the polymeric matrix and of tending to form low-solubility macrocrystals on the polymer surface. Furthermore, they do not bring about the deposition of the active ingredient, substantially in the amorphous form, which is the most soluble form especially for sparingly soluble active ingredients.

Therefore, the need for processes yielding improved accelerated release formulations is deeply felt. In particular, there is an urgent need for a process allowing a better control of the active ingredient particle size, and promoting the stable formation of large quantities of amorphous active ingredient.

SUMMARY

The following description refers to a process for the impregnation of cross-linked polymers with an active ingredient. The process is based on the use of compressed fluids, in particular $CO_2$, with antisolvent effect, and involves the steps of impregnating the polymer with an active ingredient solution, adding a compressed fluid until precipitation of the active ingredient caused by the compressed fluid antisolvent effect, removing the solvent and the compressed fluid. The process allows to obtain accelerated release pharmaceutical formulations that, compared with the formulations already known, contain larger quantities of amorphous or nanocrystalline active ingredient.

DETAILED DESCRIPTION OF THE INVENTION

Figure 1:
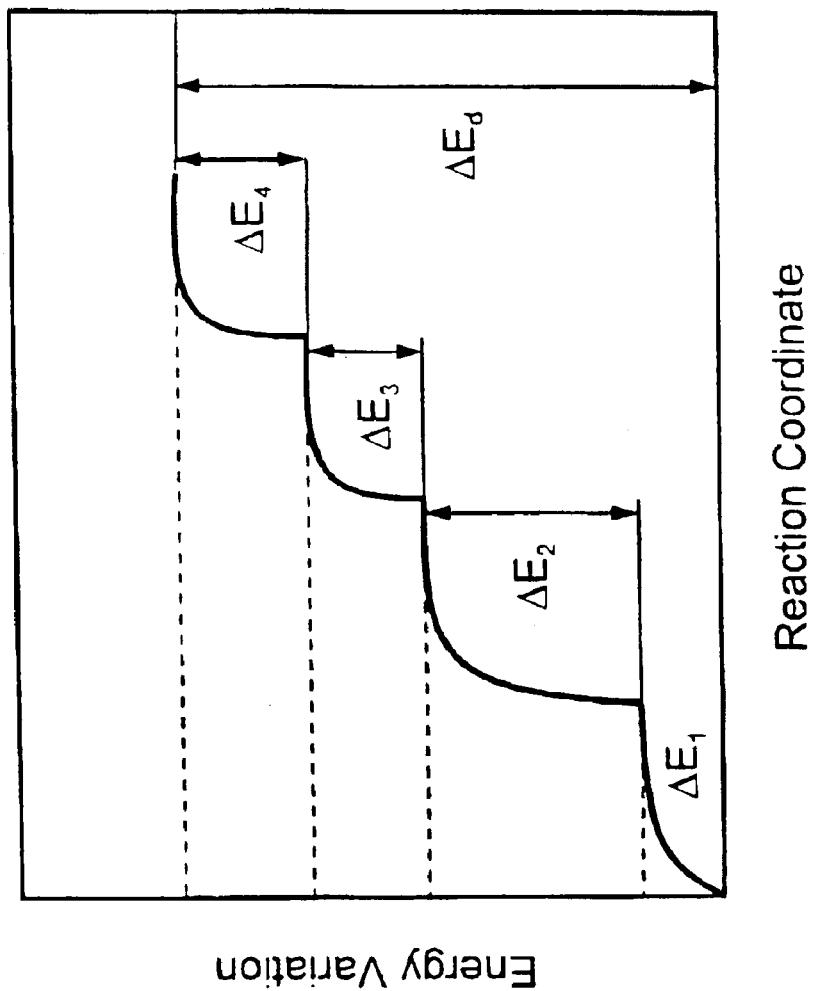
FIG. 1: energy diagram of solid phase dissolution:
$\Delta E_1$=surface interaction; $\Delta E_2$=crystal lattice dissolution
$\Delta E_3$=solvation; $\Delta E_4$=diffusion; $\Delta E_D$=total dissolution

It has now been found that accelerated release pharmaceutical formulations containing large quantities of active ingredient deposited in the amorhous form can be obtained by a process exploiting the compressed fluids capability of acting as antisolvents towards active ingredient solutions.

It is an object of the present invention to provide a process for impregnating a cross-linked polymer with an active ingredient, which consists in the following steps carried out in an appropriate reactor:
  a. swelling a cross-linked polymer with an active ingredient solution in a suitable organic solvent;
  b. feeding the reactor with a compressed fluid until reaching or exceeding the active ingredient precipitation pressure;
  c. removing the organic solvent;
  d. removing the compressed fluid.

Any pressurizable reactor can be used to perform the present process. The reactor is provided with openings suitable for solid substances loading and unloading and inlets and outlets for fluids. The equipment of the plant where the process takes place is of standard type.

The suitably thermostated reactor allows to operate at preset and controlled temperatures. The fluid inlet and outlet location is preferably such as to make the gas flow within the reactor in an upward or downward stream. The reactor bottom and top are preferably provided with metal baffles whereby the antisolvent is distributed and the solid retained.

The process is generally carried out at operating pressures in the order of 40 to 120 bar; therefore, it can be effected in conventional plants with no need of high safety standards like those for the treatment of supercritical fluids.

Step a. envisages the swelling of a cross-linked polymer with an active ingredient solution dissolved in an appropriate organic solvent.

Any cross-linked polymer may be used. In the case of pharmaceutical formulations the polymer must be biocompatible.

Exemplary cross-linked polymers are hydrophilic polymers such as cross-linked polyvinylpyrrolidone, cross-linked carboxymethylcellulose sodium salt, cross-linked polymers of cyclodextrins, cross-linked dextran, cross-linked carboxymethyl starch sodium salt and hydrophobic polymers such as cross-linked polystyrene, cross-linked acrylic acid, cross-linked polymethacrylate sodium salt.

The organic solvent selected must be capable of dissolving the active ingredient but not the polymer; furthermore, it must have swelling properties towards the polymer. Exemplary solvents are alkanes, such as cyclohexane, toluene and benzene; halogenated hydrocarbons, such as methylene chloride and chloroform; ethers, such as diethyl ether and dioxane; ketones, such as acetone; esters, such as ethyl acetate, nitrogenous compounds, such as acetonitrile, N-methyl-2-pyrrolidone and dimethylformamide; sulfurated compounds, such as dimethyl sulfoxide; alcohols, such as methanol, ethanol and 1-propanol; polyalcohols, such as ethylene glycol and tetraglycol. Preferred solvents are dipolar aprotic solvents, such as dimethylformamide, dichloromethane, dimethylsulfoxide, etc. Particularly preferred is dimethylformamide.

In general, any active ingredient may be used for the purposes of this process. The process is particularly interesting for poorly soluble active ingredients, in particular for active ingredients that tend to form crystalline aggregations of low solubility in respect of the corresponding amorphous forms. The active ingredients are typically, but not exclusively, of pharmaceutical type. An interesting group of pharmaceutical active ingredients consists of drugs of biopharmaceutical class II (as defined in "Guidance for Industry: Immediate Release Solid Oral Dosage Forms", Center for Drug Evaluation and Research at the Food and Drug Administration, 1997). Their solubility is low, but, once dissolved, their absorbability in the gastrointestinal tract is high. Exemplary drugs of this class are griseofulvin, megestrol, nimesulide, piroxicam, carbamazepine, acyclovir.

Purpose of step a. is to swell the polymer with an active ingredient solution. The solution volume added to the polymer must be sufficient for polymer swelling and at the same time must contain the quantity of active ingredient required for loading the polymer with the intended dose. The solution concentration generally ranges from 1 to 500 mg/cm$^3$, preferably from 10 to 100 mg/cm$^3$.

The maximum amount of active ingredient that may be introduced into the polymer depends on the active ingredient/solvent/polymer system used and may be determined by tests conducted beforehand. Generally, cross-linked polymers may be impregnated in an active ingredient/dry polymer ratio ranging from 1:20 to 1:0.5, preferably from 1:10 to 1:1 by weight.

Polymer swelling as per step a. may be either total or partial. Swelling is total when, in equilibrium, it does not increase in size in spite of further solvent additions. Swelling is partial when its volume ranges from 10% to 80%, preferably from 25% to 75%, in respect of the maximum swelling. To the purpose of the present process, partial swelling is preferable.

Step a. may be conducted at atmospheric pressure and, therefore, can be also implemented outside the reactor.

Step b. exploits the compressed fluid capability of dissolving in the solvents, thus reducing the solubility of substances dissolved therein (antisolvent effect). By compressed fluid it is meant a fluid at temperature and pressure conditions above its triple point, which are such as to involve the liquid and gas phases. Said conditions include fluids in the supercritical state (temperature and pressure above the critical point) and in the subcritical state (temperature and pressure below the critical point). Exemplary compressed fluids are $CO_2$, propane and hydrofluorocarbons, such as difluoromethane. Particularly preferred is $CO_2$.

In step b. the compressed fluid is added to the closed reactor, thermostatted at the operating temperature and containing the swollen polymer. Addition is preferably made at the reactor bottom: the pressure inside the reactor rises and the fluid dissolves partially in the polymer-swelling solution. Above a fixed pressure level, characteristic of each solute/solvent couple and depending on the temperature, the drug separates from the impregnating solution and precipitates into the polymer.

For each solute/solvent couple, the precipitation pressure can be easily determined beforehand. To this end, the active ingredient solution is subjected to precipitation tests conducted at increasing compressed fluid pressures, at the plant operating temperature. The same method may be utilised to determine the time required for a complete precipitation: tests may be performed in a bench-scale plant, in which the reactor is provided with a site glass for visual or instrumental checks.

The plant operating temperature usually ranges from $-20°$ C. to $80°$ C. and is preferably kept constant throughout the period in which the reactor is pressurized with the compressed fluid.

The pressure inside the reactor is maintained at values equal to or higher than the precipitation pressure until precipitation completion. Once precipitation is completed, the mass is preferably allowed to stand for a given time, e.g. 15 min, before step c. starts.

In step c. the solvent is removed from the reactor. This step is conducted at compressed fluid pressures equal to or higher than the precipitation pressure. In fact, at lower pressures the active ingredient would redissolve in the solvent and be lost during the solvent removal process.

The preferred method of solvent removal consists in the solvent siphoning and draining at the reactor bottom and/or the stripping of same by the compressed fluid flowing through the reactor.

According to a preferred method, the solvent is removed by making the compressed fluid flow under pressure within the reactor in a downward stream, whereby the solvent is pushed towards the reactor bottom. The polymer containing the precipitated drug is retained in the reactor by a porous steel baffle, whereas the solvent is stripped by the antisolvent flow.

The fluid stream consisting of antisolvent and solvent flows outside the reactor, where it may be subjected to a separation process for solvent and antisolvent recovery and recycle; in this case, the solution is sent to a separation section consisting of gravimetric and cyclonic separators in series. In separators, the solvent segregates from the antisolvent stream, as a liquid phase, by effect of the decrease in pressure and, thanks to an inertial impact, is collected on the vessels bottom to be used again in the subsequent impregnation cycles; the antisolvent is recycled to the accumulation tank and reused in the process. By said procedure, it is possible to remove most solvent.

The residual solvent is stripped by the compressed fluid preferably in an upward stream. Finally, the compressed fluid pressure may be increased to favour the mass drying.

The solvent-enriched compressed fluid is carried outside the reactor and sent to the separation section where, under appropriate temperature and pressure conditions, the two components can be separated and made available for subsequent impregnation cycles.

Step d. consists in the reactor depressurization and in the recovery of the polymer loaded with the active ingredient.

According to a preferred embodiment of the present process, at the moment of compressed fluid immission (step b) the polymer has not reached its maximum swelling: this may be obtained in particular by:

(1) removing some solvent from the swollen polymer before starting the precipitation by the compressed antisolvent effect (partial stripping);

(2) loading the polymer by two or more impregnation cycles, wherein the swelling solution volume is subdivided into the two, or more, impregnation cycles;

(3) dissolving the active ingredient in a solvent volume smaller than that required for the total polymer swelling, and using said solution as swelling solution.

According to (1) (partial stripping), step b. is preceded by solvent removal carried out as per step c. However, in this case, the solvent removal is only partial and must maintain the active ingredient concentration in the solution below the precipitation threshold. Solvent removal is preferably carried out at relatively low pressures (60 to 80 bar) and temperatures (30 to $50°$ C.) for 40 min max.

According to (2) the polymer is impregnated by two or more precipitation cycles: in this case, the solution volume containing the amount of active ingredient to be introduced into the polymer is subdivided, preferably in equal volumes, into two or more steps a. The first step a. is usually carried out at atmospheric pressure, whereas the subsequent steps a. are carried out by injecting the solution directly into the pressurized vessel.

Once the last precipitation cycle is completed, the polymer impregnated with the final quantity of active ingredient is recovered.

Procedures (1)–(3) may also be combined within a single process.

The process described herein does not involve any appreciable loss of active ingredient, which quantitatively precipitates inside the polymer in the amorphous form. The variants (1)–(3) utilising the polymer partial swelling give polymers containing from 95% to 100% approx. of active ingredient in the amorphous form and from 5% to 0% approx. in the nanocrystalline form, substantially free from crystals with size exceeding 1000 nanometres.

According to the present invention, the precipitation is to be induced by the compressed fluid antisolvent effect, i.e. above the precipitation pressure. As shown by the experimental tests described hereinafter, the precipitation induced by simple solvent removal caused by the compressed fluid stream gives products containing % amounts of the amorphous form sharply lower than those described above.

The polymers impregnated according to the invention, in particular those obtained according to the variants utilising partial swelling, are substantially free from low solubility macrocrystals deposition phenomena and, therefore, differ from the polymers impregnated according to traditional methods.

The polymer impregnated according to the invention may be conveniently formulated to prepare compositions providing an accelerated active ingredient release. In said compositions, which are typically pharmaceutical compositions for use in human and animal therapy, the impregnated polymer is used as such or mixed with suitable pharmaceutical excipients and/or diluents; in said formulations the polymer may also contain flavours, sweeteners, colouring agents, etc. Impregnated polymers according to the invention may be optionally coated with membranes modulating and/or delaying the active ingredient release. Furthermore, in the case of drugs with an amorphous form less soluble than the crystalline one, the composition shows the characteristics of a sustained release formulation.

Although the present process is mostly applied to the pharmaceutical field, it may be also used for the preparation of solid non-pharmaceutical compositions meant for releasing active ingredients in liquid environments, e.g. formulations of detergents, disinfectants, clarifiers, sweeteners, flavouring agents, etc.

For the purposes of the present invention, by active ingredient it is meant single active substances or mixtures thereof.

The following examples illustrate the claimed invention; in no event are they to be regarded as limiting the scope of the invention.

EXPERIMENTAL PART

Materials and Methods

Physically cross-linked polyvinylpyrrolidone (cross-povidone, c-PVP) was impregnated with a drug sample of biopharmaceutical group II (griseofulvin, GF). The compressed fluid used was compressed $CO_2$.

Impregnation was carried out according to four different operating procedures, the first for reference and the other three according to the present invention, i.e.:

1. precipitation by solvent removal below the precipitation pressure
2. precipitation by antisolvent effect
3. precipitation by antisolvent effect, with partial solvent removal before precipitation
4. multiple precipitation by antisolvent effect.

Procedures 2, 3 and 4 involved an incomplete polymer swelling, below the maximum swelling limit.

Figure 2:
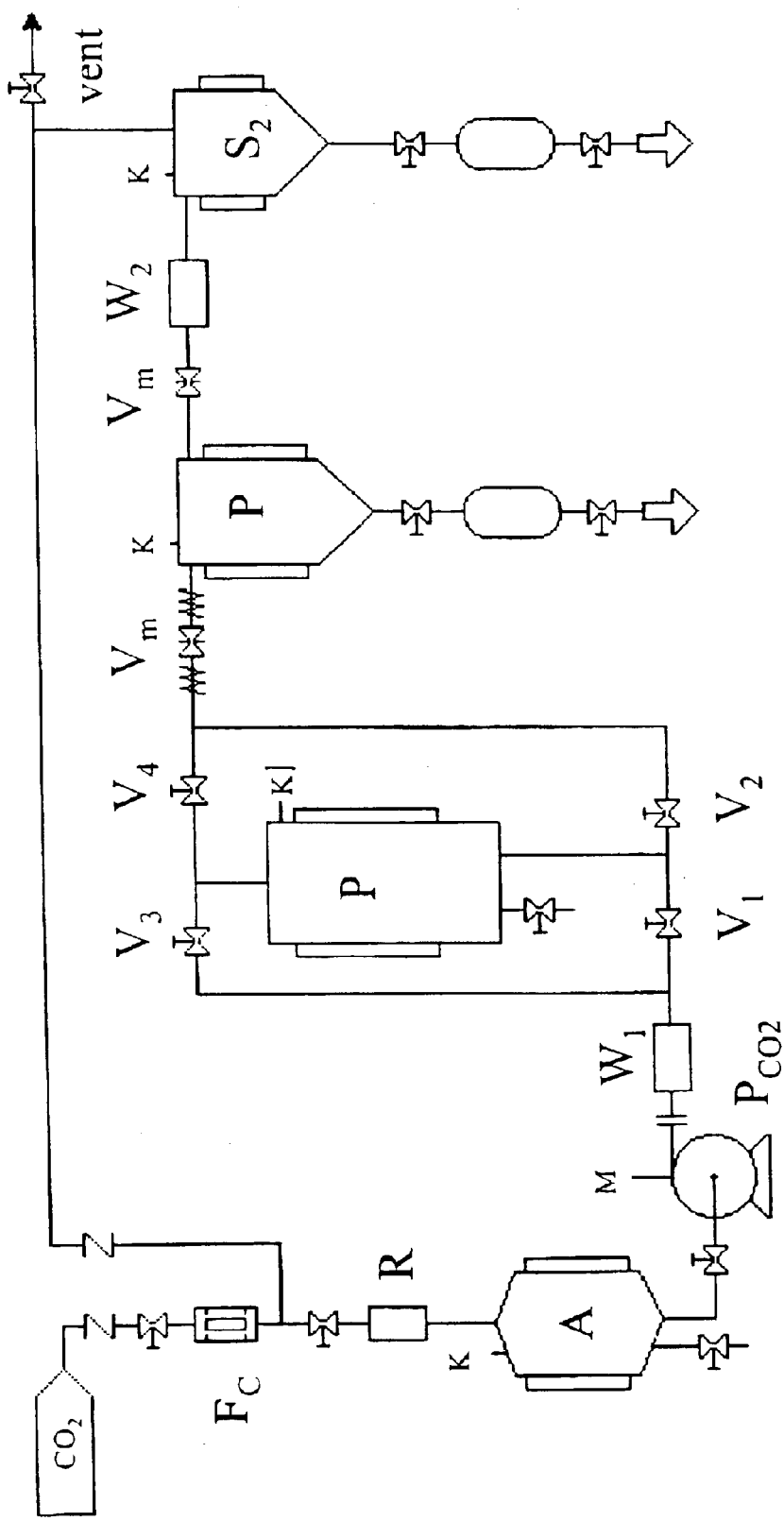
FIG. 2: layout of an impregnation pilot plant:
A=accumulation tank; FC=$CO_2$ filter; K=safety function; P=reactor; P $CO_2$=$CO_2$ pump ; R=condenser; S=separator; Vm=control valve; W=heat exchanger

The pilot plant used for the experimentation is shown in FIG. 2. The sample being examined was placed in a steel cylinder, provided with porous steel baffles at both ends to prevent the solid entrainment and the liquid ourflow during loading, and to favour the distribution of $CO_2$ during swelling and precipitation. The average porosity of the filtering baffle was 20 $\mu$m.

PVP swelling was carried out according to a traditional procedure: a GF solution (at a concentration of 100 mg/cm$^3$) in DMF or DMC solvent was poured into a mortar containing c-PVP. The system was allowed to stand in a solvent-saturated environment for 1 h. The swelling solution used amounted to 2 cm$^3$ per g of c-PVP.

1. Precipitation by Solvent Removal Below the Precipitation Pressure

The polymer-drug-solvent sample was poured into the thermostated reactor cylinders. $CO_2$ was fed from the reactor bottom at a pressure below the drug precipitation pressure. Once the preset value was reached, the system was allowed to stand for a few minutes to homogenize the swollen suspension. The solvent was then stripped from the mass by feeding $CO_2$ from the reactor bottom under isobaric and isothermal conditions for 30 min approx. The operation was carried out for further 30 min at a higher pressure until complete removal of the organic solvent. The solute precipitation was obtained.

Antisolvent $CO_2$ was fed continuously from the reactor bottom. The antisolvent residence time in the reactor was 10 min approx.

The solvent was recovered in the separation sections downstream of the reactor while $CO_2$ was condensed and recycled continuously to the accumulation tank. Once the $CO_2$ flow was stopped, the reactor was isolated and depressurized before being opened for sample recovery.

Tests were conducted with dichloromethane and dimethylformamide at 40° C. and 50° C. With regard to the pilot plant used for the experimental tests, the antisolvent flow rate was maintained at 10 kg/h. Table 1 shows the operating conditions observed during the experimental tests.

TABLE 1

| Sample | Temperature, ° C. | Stripping pressure, bar | Washing pressure, bar |
| --- | --- | --- | --- |
| GF-DCM 01 | 40 | 52 | 80 |
| GF-DCM 02 | 50 | 65 | 100 |
| GF-DMF 01 | 40 | 70 | 100 |
| GF-DMF 02 | 50 | 90 | 120 |

Figure 3:
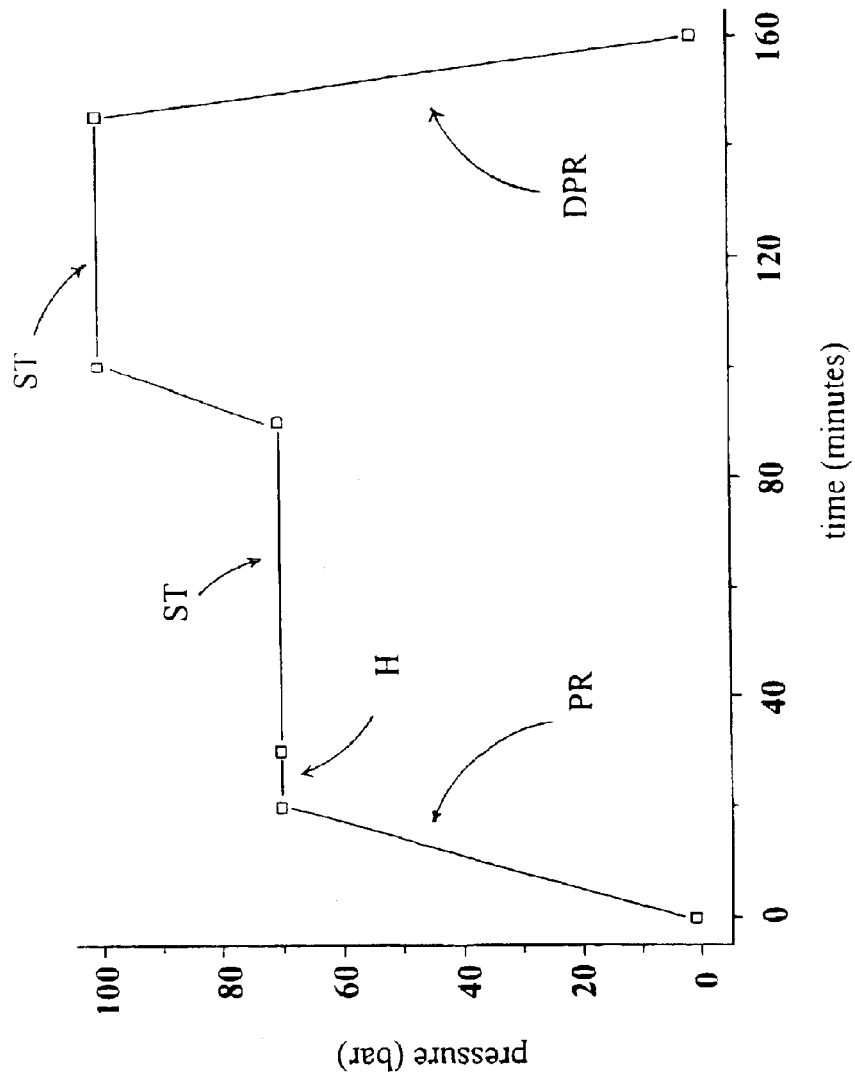
FIG. 3: precipitation by solvent removal below precipitation pressure

Process steps are shown in FIG. 3.

2. Precipitation by Antisolvent Effect

The polymer-drug-solvent sample was poured into the thermostated reactor cylinders. Compressed $CO_2$ was fed from the reactor bottom until exceeding the drug precipitation pressure. Once said value was reached, the system was allowed to stand for a few minutes. $CO_2$ was then caused to flow and the liquid was siphoned and drained for 15 min approx. The solvent was stripped by feeding $CO_2$ from the reactor top under isobaric and isothermal conditions and subsequently by raising the $CO_2$ pressure. The operation was carried out until complete removal of the organic solvent. The solvent was recovered in two tanks located downstream of the reactor, while $CO_2$ was condensed and continuously recycled to the accumulation tank. Once the $CO_2$ flow was stopped, the reactor was isolated and depressurized before being opened for sample recovery.

Tests were conducted with dimethylformamide at 12° C. and 40° C. With regard to the pilot plant used for the experimental tests, the antisolvent flow rate was maintained at 10 kg/h. Table 2 shows the operating conditions observed during the experimental tests.

TABLE 2

| Sample | Temperature, ° C. | Precipitation pressure, bar | Washing pressure, bar |
| --- | --- | --- | --- |
| GF-DMF 03 | 40 | 90 | 110 |
| GF-DMF 04 | 12 | 80 | 110 |

Figure 4:
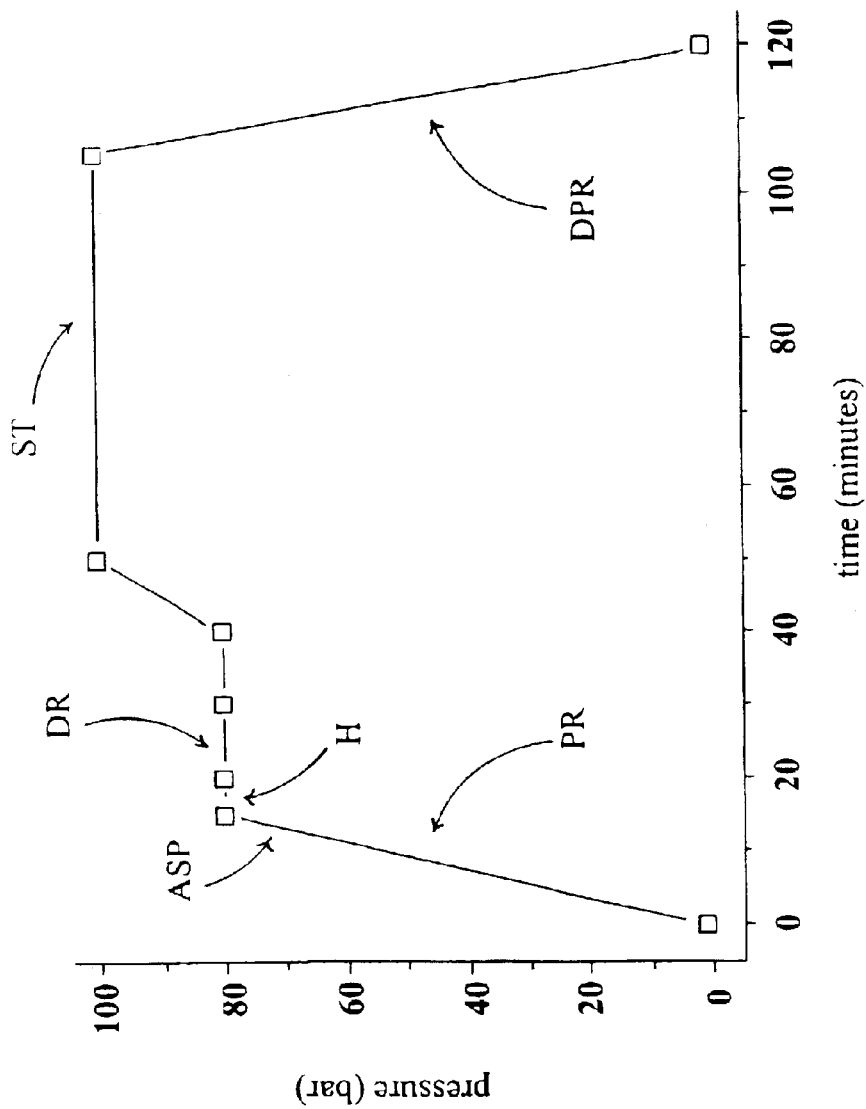
FIG. 4: precipitation by antisolvent effect

Process steps are shown in FIG. 4.

3. Precipitation by Antisolvent Effect, with Partial Solvent Removal Before Precipitation The polymer-drug-solvent sample was poured into the thermostated reactor cylinder. Compressed $CO_2$ was fed from the reactor bottom at a constant temperature to a preset pressure value below the precipitation pressure.

Once the preset value was reached (stripping pressure), $CO_2$ was fed in an upward stream under isobaric and isothermal conditions until removing solvent excess of the polymer swelling limit.

Flow configuration being kept unaltered, the pressure of $CO_2$ was raised to exceed the precipitation value. Once the preset value was reached, the system was allowed to stand for a few minutes; the $CO_2$ flow was reversed and the liquid was siphoned and drained for 15 min.

Once draining was completed, $CO_2$ was caused to flow upward by antisolvent feeding from the reactor bottom under isothermal conditions and the $CO_2$ pressure raising for the solvent final stripping. The operation was carried out until complete removal of the organic solvent.

The solvent was recovered in two separators downstream of the reactor, while $CO_2$ was condensed and continuously recycled to the accumulation tank. Once the $CO_2$ flow was stopped, the reactor was isolated and depressurized before being opened for sample recovery.

Tests were conducted with dimethylformamide at 40° C. and 50° C. With regard to the pilot plant used for the experimental tests, the antisolvent flow rate was maintained at 10 kg/h. Table 3 shows the operating conditions observed during the experimental tests.

TABLE 3

| Sample | Temperature, ° C. | Stripping pressure (bar) and stripping time | Precipitation pressure, bar | Washing pressure, bar |
|---|---|---|---|---|
| GF-DMF 05 | 50 | 80, (90 min) | 100 | 120 |
| GF-DMF 06 | 50 | 80, (60 min) | 100 | 120 |
| GF-DMF 07 | 50 | 80, (40 min) | 100 | 120 |
| GF-DMF 08 | 40 | 70, (60 min) | 90 | 110 |
| GF-DMF 09 | 40 | 70, (40 min) | 90 | 110 |

Figure 5:
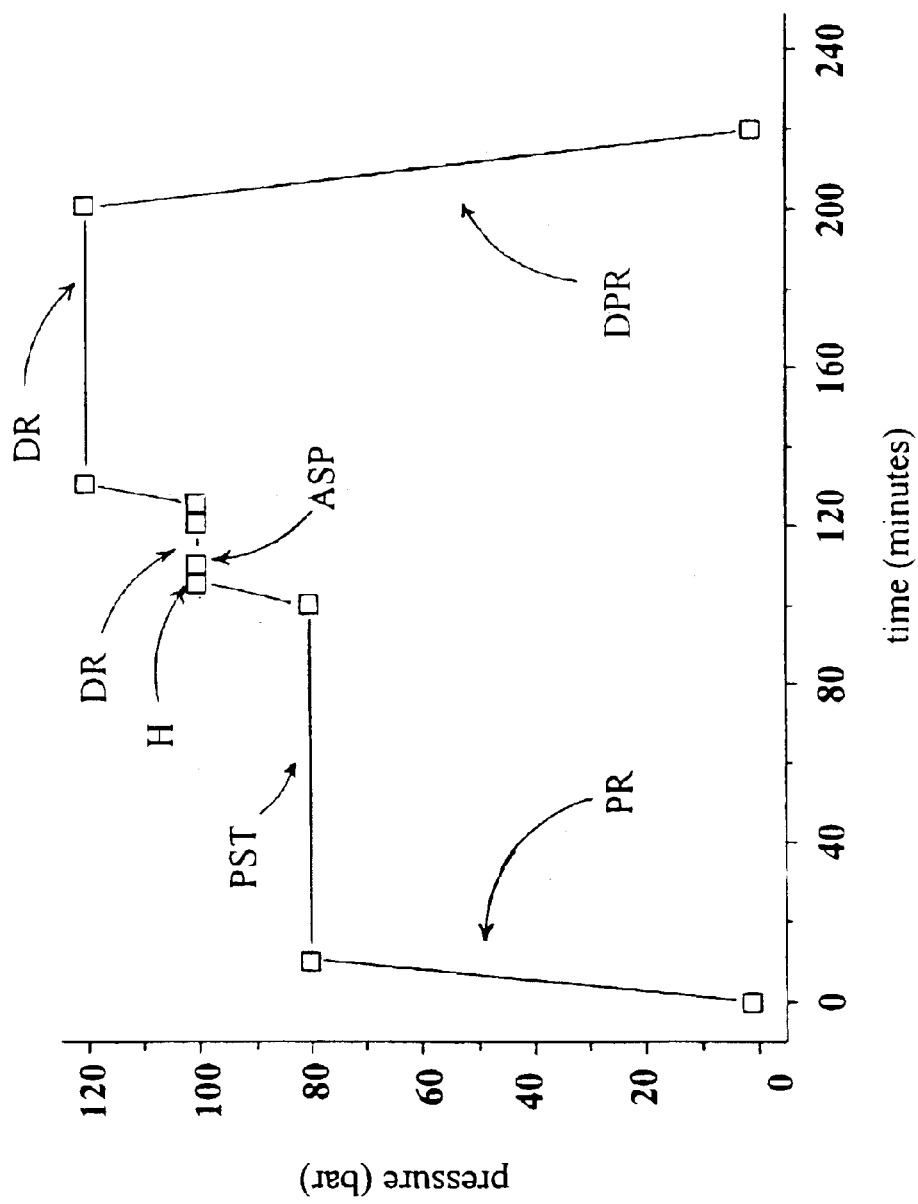
FIG. 5: precipitation by antisolvent effect, with partial solvent removal prior to precipitation

Process steps are shown in FIG. 5.

4. Multiple Precipitation by Antisolvent Effect

The polymer was partially swollen with an amount of a drug-solvent solution below the swelling limit, at atmospheric pressure.

The sample was poured into the termostated reactor cylinder. Compressed $CO_2$ was fed from the reactor bottom at constant temperature to a preset pressure value below the precipitation pressure.

Once homogenization was completed, the $CO_2$ pressure was raised until exceeding the drug precipitation value. The system was allowed to stand for a few minutes; the $CO_2$ flow was reversed and the liquid was siphoned and drained for 15 min.

Once draining was completed, the $CO_2$ flow was reversed again by antisolvent feeding from the reactor bottom under isothermal conditions and the reactor pressure was decreased below the precipitation value. At this point, the polymer was added with the rest of the swelling solution by injection under pressure by means of a liquid pump. The system was allowed to homogenise for 15 min and fresh $CO_2$ was fed to limit the decrease in pressure. The subsequent steps were precipitation, siphoning, draining, partial depressurization as previously described. Once the whole swelling solution was fed to the reactor under pressure and draining was completed, the $CO_2$ flow was reversed with antisolvent feeding from the reactor bottom under isothermal conditions; the $CO_2$ pressure was raised for the solvent final stripping. The operation was carried out until complete removal of the organic solvent.

The solvent was recovered in two separators downstream of the reactor, while $CO_2$ was condensed and continuously recycled to the accumulation tank. Once the $CO_2$ flow was stopped, the reactor was isolated, depressurized and opened for sample recovery.

Tests were conducted with dimethylformamide at 40° C. and 50° C. With regard to the pilot plant used for the experimental tests, the antisolvent flow rate was maintained at 10 kg/h. Table 4 shows the operating conditions observed during the experimental tests.

TABLE 4

| Sample | Temperature, ° C. | Precipitation pressure, bar | Washing pressure, bar |
|---|---|---|---|
| GF-DMF 10 | 50 | 100 | 120 |
| GF-DMF 11 | 40 | 90 | 110 |

Figure 6:
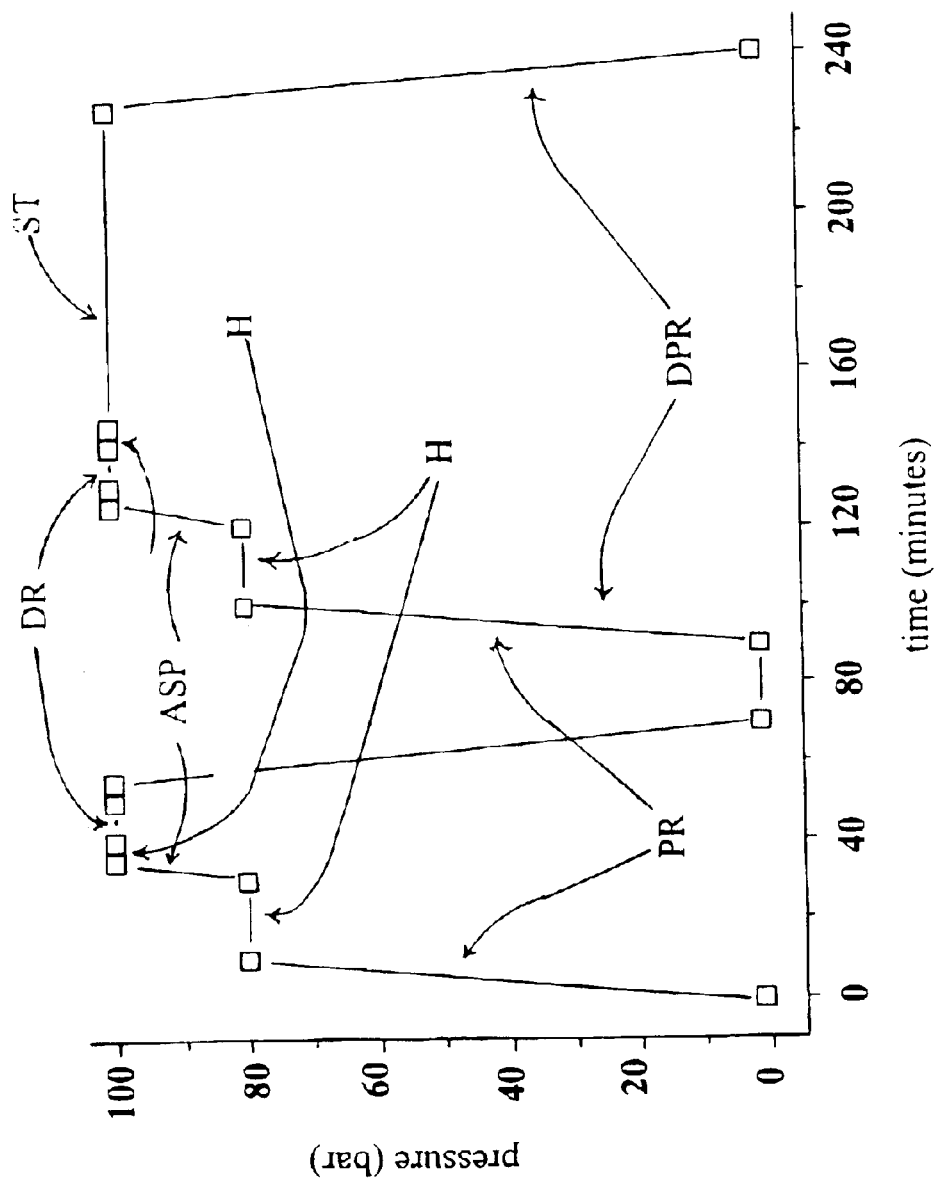
FIG. 6: multiple precipitation by antisolvent effect:
PR=pressurization
ASP=antisolvent precipitation
H=homogenization
DR=draining, siphoning
ST=stripping
PST=partial stripping
DPR=depressurization

Process steps are shown in FIG. 6.

Results

Determination of the Drug Quantity in the Polymer

Griseofulvin content per g of cross-linked polyvinylpyrrolidone was determined by extraction with anhydrous methanol. The drug-polymer sample (100 mg) was added with methanol (50 cm$^3$). The suspension was then sonicated for 15 min, stirred for 20 min, filtered through a Sartorius 18406-25 membrane and diluted with methanol. The concentration of the resulting solution was analysed spectrophotometrically (Perkin Elmer spectophotometer, Lambda 20 type) at a wavelength of 291.2 nm. The quantity of griseofulvin present in 100 mg of analysed sample was calculated by the following equation:

$$W_G = C_G * \text{Dilution} * 50$$

where $W_G$ is the drug mass extracted from the sample, $C_G$ is the concentration determined by spectrophotometric analysis and 50 are the cm$^3$ of methanol used for extraction.

The quantity of analysed sample (100 mg) and the quantity of drug present in the sample ($W_G$) being known, the % amount of griseofulvin per g of polymer (T %) was calculated by the following equation:

$$T\ (\%) = W_G / (100 - W_G) * 100$$

Charaterization of the Drug Physical State in Drug-Polymer Systems

The systems prepared according to the present invention are characterised by a high dispersion degree of drug molecules in the polymeric lattice.

The drug dispersion was evaluated through the determination of the residual crystallinity and position in respect of the polymeric particles, by differential scanning calorimetry (DSC).

Figure 7:
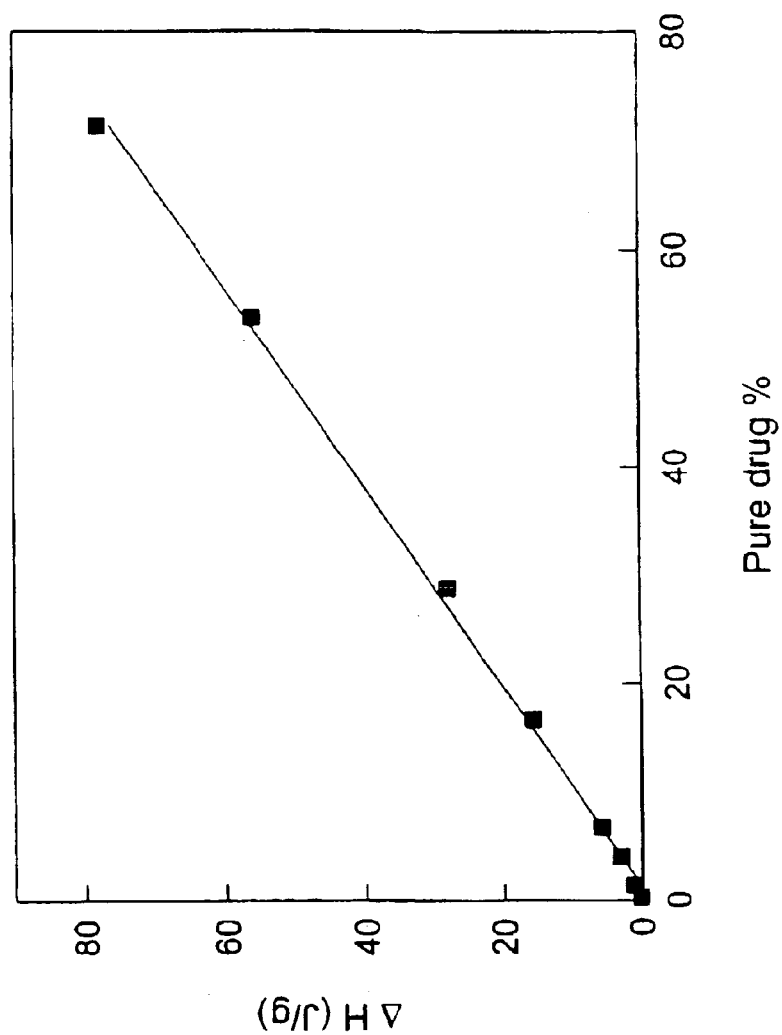
FIG. 7: correlation between the specific melting enthalpy of griseofulvin in a physical mixture with cross-povidone and pure griseofulvin % content (100% crystalline)

The % residual crystallinity was calculated by measuring the specific melting enthalpy and by the following equation:

$$\%\ C = (\Delta H_a * 100) / (1.084 * T\ (\%))$$

where % C is the % crystallinity of the drug, $\Delta H_a$ is the apparent specific melting enthalpy determined by DSC, T (%) is the % amount of drug in the system, and the constant 1.084 is the angle coefficient of the calibration straightline obtained by measuring the melting enthalpy in preconstituted drug-polymer physical mixtures having a known drug content (see FIG. 7).

The balance to 100 shown in Table 5 is the percent amount of amourphous polymer, which, therefore, is molecularly dispersed in the polymeric lattice (cf. "Influence of polymer characteristics on drug loading into cross-povidone", F. Carli, I. Colombo, L. Magarotto, A. Motta, and C. Torricelli, International Journal of Pharmaceutics, 33, 115, 1986).

Furthermore, the crystalline forms present in samples obtained according to the invention could be located, in respect of the polymeric particles, by determining the melting temperature of residual crystals and applying the thermodynamic model correlating the melting temperature with the bend radius of the solid-liquid phase (crystallites size, cf.

"Differential scanning calorimetry of drug solid dispersion in cross-linked polymers", I. Colombo, F. Carli and L. Magarotto, 4th International Conference on Pharmaceutical Technology, Paris, June 1986):

$$T_F - T_M = 2/\Delta S_M [-v_S(\gamma_{SL}/R_{SL}) - (v_S - v_L)(\gamma_{LG}/R_{LG})]$$

where $T_F$ is the melting temperature of drug crystals in the sample, $T_M$ is the melting temperature of the substance as such (crystals of the starting raw material): for griseofulvin, $T_M = 219.5°$ C.; $v_S$ and $v_L$ are the molar volume of the solid and liquid phase, respectively; $\gamma_{SL}$ e $\gamma_{LG}$ are the solid-liquid and the liquid-gas interface tension, respectively; $R_{LG}$ is the bend radius of the liquid-gas interface (representing the average size of intermolecular empty spaces in the polymeric lattice) and $R_{SL}$ is the bend radius of the solid-liquid interface (representing the average dimension of the crystalline form).

When the melting temperature of the drug residual crystals is lower than that of the raw material, the inhibition to the crystallite growth is to be attributed to the space constraint only, i.e. to the macromolecules tridimensional lattice inside the single polymeric particles. Furthermore, since the internodal distances in the polymeric lattice are in the order of some tenths of nanometres (cf A. Sanner et al., Proceeding of the International Symposium on Povidone, Lexington, USA, 1983), the residual crystals located inside the polymeric particles must have dimensions in the order of nanometres (nanocrystals).

Therefore, the melting temperature of the crystalline form may be used to define whether the phase is located inside ($T_F < T_M$) or outside ($T_F = T_M$) the polymeric particles. In the case of griseofulvin, the lower $T_F$ is in respect of 219.5° C., the smaller is the crystal size: the high nanonization of the crystals indicates that the precipitation predominantly takes place inside and not on the surface of the polymeric particles.

The data of Table 5 show that the drug dispersion degree (% amount of the amorphous form) obtained by stripping only (procedure 1) is extremely variable and always below 85%; furthermore, the crystalline form still present is located outside the carrier particles ($T_F = T_M$). Similar results seem to be obtained by the procedure envisaging partial stripping followed by precipitation by antisolvent effect (procedure 3); however, by operating at relatively low pressures and temperatures (60 to 80 bar and 30 to 50° C., for 40 min max.) it is possible to obtain systems containing 85% min. of drug in the amorphous form. By means of the antisolvent effect only (single and multiple GASP), systems containing large amounts of drug in the amorphous form were obtained: 85% min. in the case of single cycle precipitation and 95% min. in the case of double precipitation, with a reduction in or complete elimination of crystalline forms outside the polymeric particles. Therefore, the method used allows the obtainment of particle polymeric systems with a large % amount of drug in the amourphos phase and a drastic reduction, or a complete elimination of the presence of the drug outside the particles.

TABLE 5

| Sample | Method | Content, (%) | M.T., ° C. | $\Delta H_a$, J/g | % amorhous |
|---|---|---|---|---|---|
| GF-DMF 01 | 1 | 16.9 | 219.5 | 2.63 | 84.4 |
| GF-DMF 02 | 1 | 15.8 | 219.7 | 7.77 | 52.3 |
| GF-DCM 01 | 1 | 24.2 | 218.6 | 5.25 | 78.6 |
| GF-DCM 02 | 1 | 27.1 | 219.3 | 8.97 | 59.4 |
| GF-DMF 03 | 2 | 15.9 | 219.6 | 0.46 | 97.1 |
| GF-DMF 04 | 2 | 14.0 | 219.6 (ext) 187.9 (int) | 0.20 (ext) 1.78 (int) | 86.2 (tot) |
| GF-DMF 05 | 3 | 15.5 | 220.3 | 5.06 | 68.3 |
| GF-DMF 06 | 3 | 17.2 | 219.9 | 5.97 | 62.2 |
| GF-DMF 07 | 3 | 15.5 | 219.6 | 2.17 | 86.5 |
| GF-DMF 08 | 3 | 16.7 | 219.4 | 4.34 | 75.2 |
| GF-DMF 09 | 3 | 18.2 | 219.1 | 1.51 | 92.1 |
| GF-DMF 10 | 4 | 16.0 | 219.6 (ext) 208.6 (int) | 0.25 (ext) 0.22 (int) | 97.2 (tot) |
| GF-DMF 11 | 4 | 15.9 | 219.6 (ext) 208.5 (int) | 0.49 (ext) 0.28 (int) | 95.3 (tot) |

What is claimed is:

1. A process for impregnating a cross-linked polymer with an active ingredient to obtain accelerated release pharmaceutical formulations, comprising the following steps, carried out in the order indicated:
   a. swelling a cross-linked polymer with a solution of the active ingredient in an organic solvent, wherein said organic solvent is capable of dissolving the active ingredient but not the polymer and has swelling properties towards the polymer;
   b. adding, into a closed reactor, to the swollen polymer/active ingredient/solvent mixture obtained in step a) a compressed fluid, which is an antisolvent for the active ingredient, until reaching a pressure equal to or higher than the precipitation pressure of said active ingredient, thereby causing precipitation of the active ingredient into the polymer;
   c. removing the organic solvent from the reactor while maintaining the pressure at values equal to or higher than the precipitation pressure of said active ingredient; and
   d. removing the compressed fluid from the reactor.

2. The process of claim 1 wherein, in step a., a polymer that is only partially swollen is obtained.

3. The process of claim 2 wherein, in step a., the polymer is first swollen with the solution of the active ingredient in the organic solvent and then the organic solvent is partially removed from the swollen polymer, maintaining the concentration of the active ingredient in solution below the precipitation threshold.

4. The process of claim 2 wherein the polymer is impregnated by repeating steps a.–d. and wherein the active ingredient solution is subdivided into two portions, to be used in the first and in the second step a., respectively.

5. The process of claim 4 wherein the two solution portions have an equal volume.

6. The process of claim 1 wherein in, step c., the organic solvent is removed by compressed fluid stream through the reactor and/or by solvent siphoning and draining.

7. The process of claim 1 wherein the active ingredient concentration in the solution ranges from 1 mg/cm$^3$ to 500 mg/cm$^3$ and the active ingredient/dry polymer ratio ranges between 1:20 and 1:0.5 by weight.

8. The process of claim 1 wherein the active ingredient that impregnates the cross-linked polymer is deposited by at least 85% in the amorphous form in respect of the total active ingredient deposited in the polymer.

9. The process of claim 1 wherein the active ingredient is a drug belonging to the biopharmaceutical class II.

10. The process of claim 9 wherein the active ingredient is selected from the group consisting of griseofulvin, megestrol, nimesulide, piroxicam, carbamazepine, acyclovir.

11. The process of claim 1 wherein the compressed fluid is $CO_2$, propane or a hydrofluorocarbon.

12. The process of claim 1 wherein the organic solvent is selected from cyclohexane, toluene, benzene, methylene chloride, chloroform, diethyl ether, dioxane, acetone, ethyl acetate, acetonitrile, N-methyl-2-pyrrolidone, dimethylformamide, dimethyl sulfoxide, methanol, ethanol, 1-propanol, ethylene glycol and tetraglycol.

13. The process of claim 1 wherein the cross-linked polymer is selected from cross-linked polyvinylpyrrolidone, cross-linked carboxymethylcellulose sodium salt, cross-linked polymers of cyclodextrins, cross-linked dextran, cross-linked carboxymethyl starch sodium salt, cross-linked polystyrene, cross-linked acrylic acid and cross-linked polymethyl methacrylate sodium salt.

14. A process for impregnating a cross-linked polymer with an active ingredient to obtain an impregnated polymer containing a large percentage of active ingredient into the amorphous state and low amounts or absence of crystalline active ingredient on the surface of the polymer particles and comprising the following steps, carried out in the order indicated:

a. swelling a cross-linked polymer with a solution of the active ingredient in an organic solvent, wherein said organic solvent is capable of dissolving the active ingredient but not the polymer and has swelling properties towards the polymer;

b. adding, into a closed reactor, to the swollen polymer/active ingredient/solvent mixture obtained in step a., a compressed fluid, which is an antisolvent for the active ingredient, until reaching a pressure equal to or higher than the precipitation pressure of said active ingredient, thereby causing precipitation of the active ingredient into the polymer;

c. removing the organic solvent from the reactor while maintaining the pressure at values equal to or higher than the precipitation pressure of said active ingredient; and d. removing the compressed fluid from the reactor.

* * * * *

UNITED STATES PATENT AND TRADEMARK OFFICE
CERTIFICATE OF CORRECTION

PATENT NO. : 6,913,779 B2
DATED : July 5, 2005
INVENTOR(S) : Italo Colombo et al.

It is certified that error appears in the above-identified patent and that said Letters Patent is hereby corrected as shown below:

Title page,
Item [75], Inventors, change "Padua" to -- Padova --.

Signed and Sealed this

Thirtieth Day of August, 2005

JON W. DUDAS
*Director of the United States Patent and Trademark Office*